(12) United States Patent
West

(10) Patent No.: US 11,607,505 B1
(45) Date of Patent: Mar. 21, 2023

(54) WEARABLE INJECTOR WITH STERILITY SENSORS

(71) Applicant: Fresenius Kabi Deutschland GmbH, Bad Homburg (DE)

(72) Inventor: Sharon D. West, Elkins Park, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/180,105

(22) Filed: Feb. 19, 2021

(51) Int. Cl.
| | | |
|---|---|---|
| *A61M 5/50* | (2006.01) | |
| *A61M 5/142* | (2006.01) | |
| *A61K 38/18* | (2006.01) | |

(52) U.S. Cl.
CPC ........... *A61M 5/5086* (2013.01); *A61K 38/18* (2013.01); *A61M 5/14248* (2013.01); *A61M 2205/581* (2013.01); *A61M 2205/582* (2013.01); *A61M 2205/583* (2013.01)

(58) Field of Classification Search
CPC ............ A61M 5/5086; A61M 5/14244; A61M 5/14248; A61M 2005/14252; A61M 2005/14268
See application file for complete search history.

(56) References Cited

U.S. PATENT DOCUMENTS

| | | | |
|---|---|---|---|
| 2003/0167036 | A1 | 9/2003 | Flaherty |
| 2009/0156990 | A1* | 6/2009 | Wenger .................. G06F 16/60 604/67 |
| 2012/0010594 | A1 | 1/2012 | Holt et al. |
| 2015/0119804 | A1* | 4/2015 | Seeley ................ A61M 5/1413 604/151 |
| 2015/0374919 | A1 | 12/2015 | Gibson |
| 2016/0038689 | A1 | 2/2016 | Lee et al. |
| 2016/0199574 | A1 | 7/2016 | Ring et al. |
| 2016/0296704 | A1 | 10/2016 | Gibson |
| 2016/0354555 | A1 | 12/2016 | Gibson et al. |
| 2017/0119969 | A1 | 5/2017 | McCullough et al. |
| 2017/0124284 | A1* | 5/2017 | McCullough ..... A61M 5/31501 |
| 2017/0147787 | A1 | 5/2017 | Albrecht et al. |
| 2017/0182253 | A1 | 6/2017 | Folk et al. |
| 2017/0340837 | A1 | 11/2017 | Nazzaro et al. |
| 2017/0361015 | A1 | 12/2017 | McCullough |

(Continued)

FOREIGN PATENT DOCUMENTS

| | | |
|---|---|---|
| WO | 2018081234 A1 | 5/2018 |
| WO | 2018183039 A1 | 10/2018 |

(Continued)

*Primary Examiner* — Amber R Stiles
*Assistant Examiner* — Leah J Swanson
(74) *Attorney, Agent, or Firm* — Cook Alex Ltd.

(57) ABSTRACT

An on-body drug delivery device having a housing and a cartridge removably attachable to the housing. The cartridge comprises: a drug chamber, a piston received in the drug chamber movable from a first, initial position to a second position, an actuation device for moving the piston from the first position to the second position, and at least one breakable sterility sensor circuit formed by attachment of the cartridge to the housing, the circuit being closed when the cartridge is properly attached to the housing and broken if the cartridge is not properly attached to the housing or removed from the housing after being attached thereto, and/or the circuit being broken if the piston is not in the initial position when the cartridge is first attached to the housing.

25 Claims, 10 Drawing Sheets

(56) References Cited

U.S. PATENT DOCUMENTS

| | | | |
|---|---|---|---|
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0193554 A1* | 7/2018 | Meehan ............ A61M 5/14248 |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani et al. |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1 | 12/2019 | Damestani et al. |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0322793 A1 | 10/2020 | Yang |
| 2020/0338271 A1 | 10/2020 | Harris et al. |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

* cited by examiner

WEARABLE INJECTOR WITH STERILITY SENSORS

BACKGROUND

Field of the Disclosure

The present disclosure relates to drug delivery/infusion devices. More particularly, the present disclosure relates to devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provide power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with gears 60 and 64 as a singled, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, it is important to ensure that the sterility of the system has been maintained, and that sterility has not been compromised due to, e.g., prior use. Thus, it would be advantageous to provide medical infusion devices with systems that prevent use of the infusion device if sterility has been compromised and alert the healthcare professional and/or patient of the non-sterile condition.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, an on-body drug delivery device is provided that comprises a housing and a cartridge removably attachable to the housing. The cartridge further comprises a fillable drug chamber, a piston received in the drug chamber movable between a first, initial position and a second position, an actuation device for moving the piston between the first position and the second position, and at least one breakable sterility sensor circuit formed by attachment of the cartridge to the housing, the circuit being closed when the cartridge is properly attached to the housing and broken if the cartridge is not properly attached to the housing or removed from the housing after being attached thereto; and/or the circuit being broken if the piston is not in the initial position when the cartridge is first attached to the housing.

In a second aspect, the piston further comprises one or more contact points that close the sterility sensor circuit when the piston is in the initial position.

In a third aspect, the drug delivery device comprises a lock actuated when the sterility circuit is broken to prevent operation of the drug delivery device.

In a fourth aspect, the drug delivery device is further configured to cause a signal to be emitted if the sterility sensor circuit is broken.

In a fifth aspect, the signal is one or more of a tactile signal, an audible signal or a visual signal that is emitted by the drug delivery device.

In a sixth aspect, the device is configured to cause the signal to be emitted by a separate device, such as a cell phone.

These and other aspects of the present subject matter are set forth in the following detailed description of the accompanying drawings.

BRIEF DESCRIPTION OF THE DRAWINGS

FIGS. 7a and 7b are perspective views of a drug delivery device in which a cartridge containing the drug reservoir includes breakable sterility sensor circuits formed between the side walls of the reservoir and a plunger contained within the reservoir, with the circuit shown as intact in FIG. 7a and broken in FIG. 7b due to movement of the plunger from the position shown in FIG. 7a.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

The methods and devices described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

Figure 1:
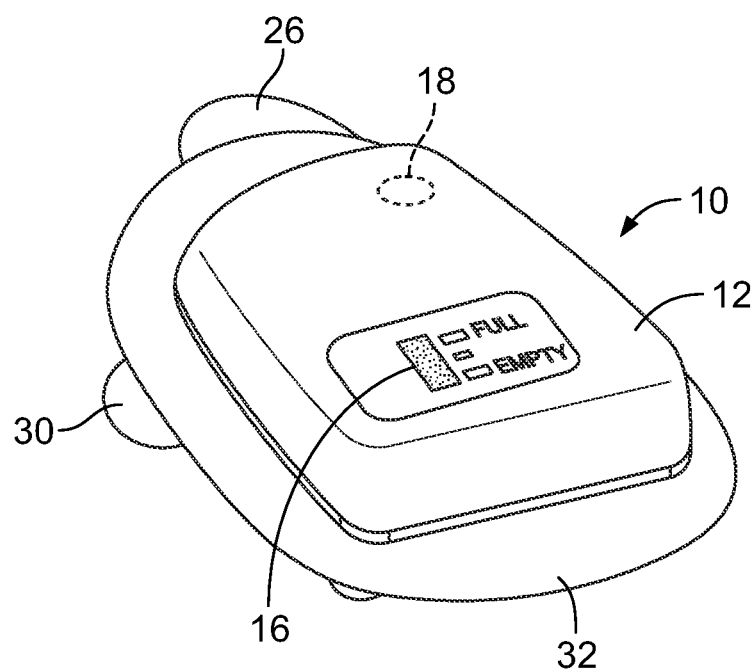
FIG. 1 is a top perspective view of a drug delivery device according to conventional design.
Figure 2:
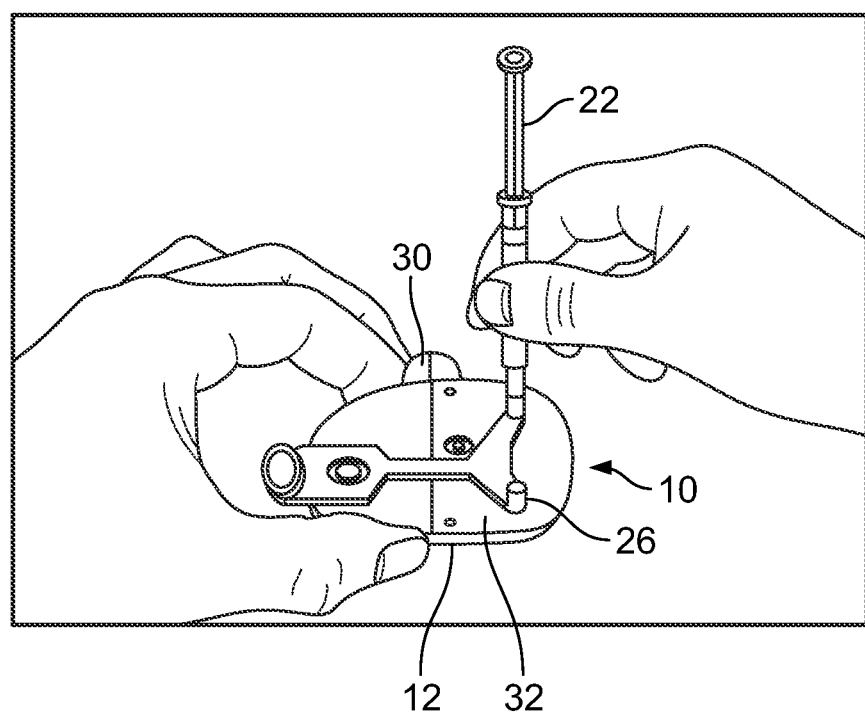
FIG. 2 is a bottom perspective view of the drug delivery device of FIG. 1.
Figure 3:
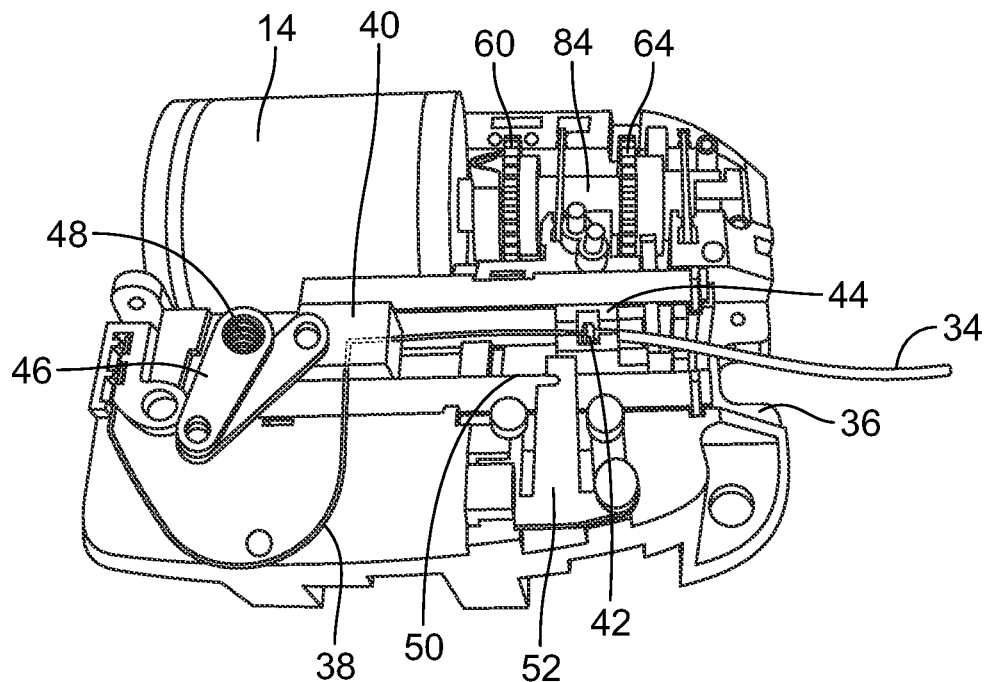
FIG. 3 is a top perspective view of the interior components of the drug delivery device of FIG. 1.
Figure 4:
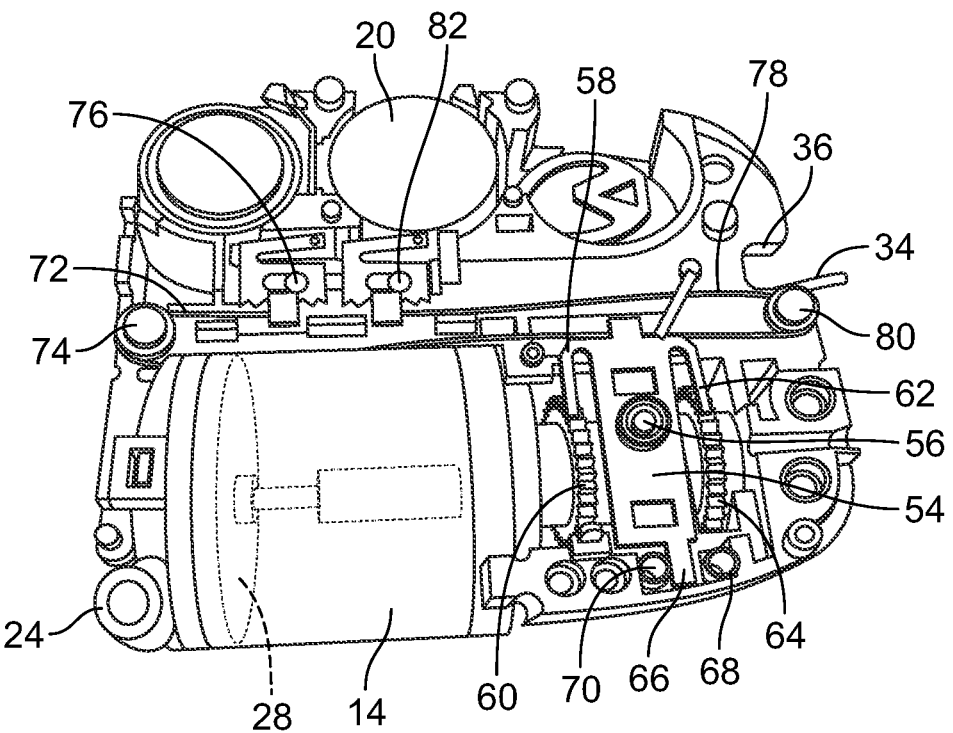
FIG. 4 is a bottom perspective view of the interior components of the drug delivery device of FIG. 1.
Figure 5:
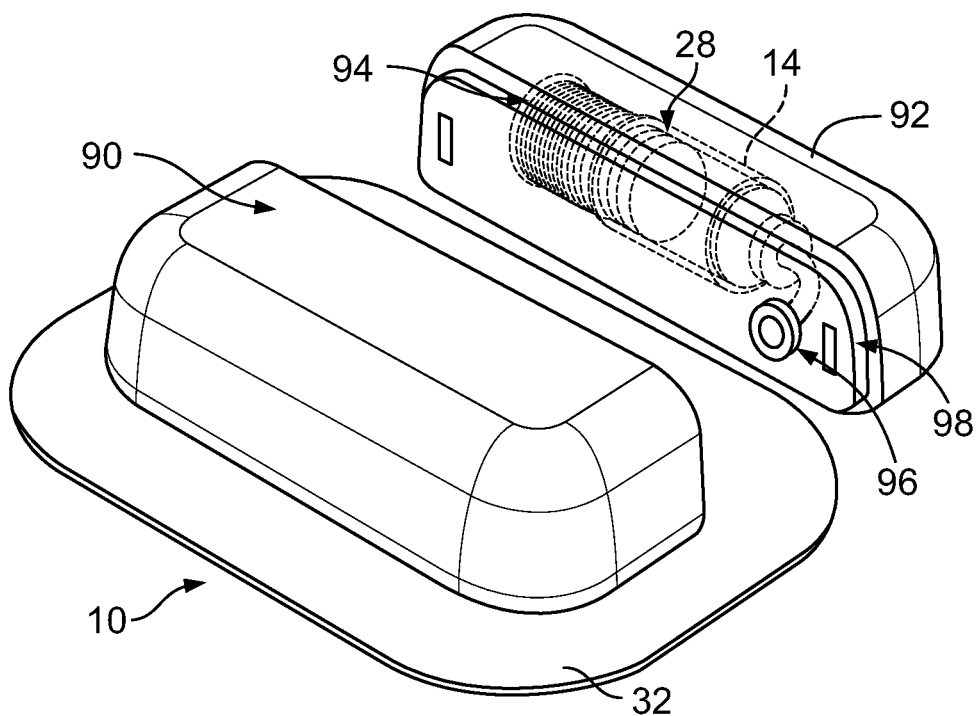
FIG. 5 is an exploded perspective view of a drug delivery device embodying the aspects of the present application.
Figure 6:
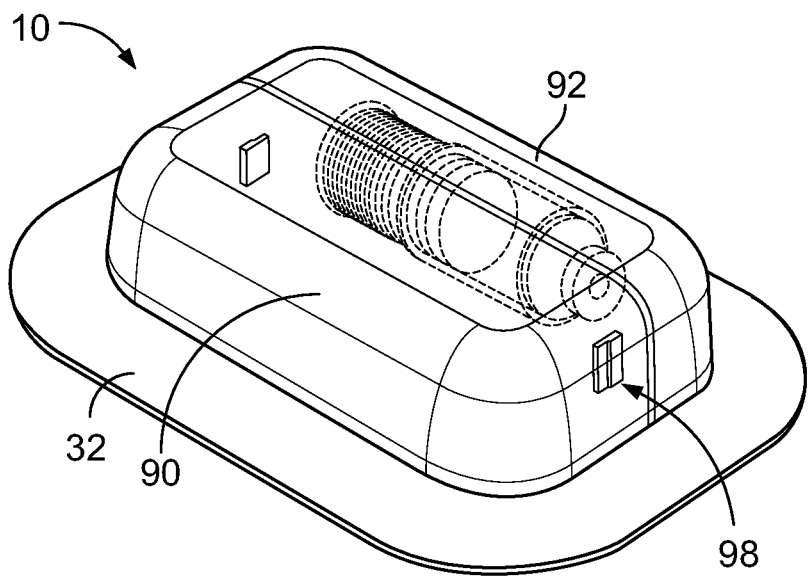
FIG. 6 is a perspective view of the assembled drug delivery device of FIG. 5.

In keeping with the present disclosure, and with reference to FIGS. 5 and 6, the drug delivery/infusion device 10 has a modular construction and comprises a main body 90 that houses many of the electro-mechanical components of the device and a removable cartridge 92 that is pre-filled and/or refillable with a drug. The removable cartridge 92 permits re-filling and reuse of the infuser without having to remove it from the patient after the initial attachment, and permits the device to be used to deliver more than one type of drug. In cases where a drug must be refrigerated prior to use, a separable pre-filled cartridge 92 also facilitates storage of the drug apart from the main body 90, which may be stored at room temperature, thus reducing the amount of refrigerated storage space required.

The cartridge further comprises a pre-filled drug chamber/reservoir 14, a piston/plunger 28, and a structure for pressurizing the drug held within the chamber for delivery to the patient. As illustrated in FIG. 6, a spring 94 is employed for pressurizing the drug, although other mechanisms for pressurizing the drug may be employed without departing from the scope of the present disclosure. A seal 96 on the cartridge 92 keeps the drug held within the chamber 14 sterile prior to attachment of the cartridge 92 to the main body 90, with the seal 96 being pierced upon attachment of the cartridge to the main body.

A mechanically- or electrically-actuated valve in the main body (not seen) serves to start, stop, and otherwise regulate flow of the drug from the infuser. The removable cartridge 92 is coupled to the main body 90 by means of, e.g., a spring-loaded latch 98 that may be locked out during infusion to prevent premature removal.

With a cartridge-based system such as that disclosed in FIGS. 5 and 6, it is important to ensure the sterility of the cartridge, as well as the contents of the drug chamber prior to its attachment to the main body, and (in some cases) ensure against the attachment to a main body of a cartridge that had been subject to prior use. To this end, one or more conductive sterility sensor circuits may be formed at various locations within the cartridge, between the cartridge and the main body, or both within the cartridge and between the cartridge and the main body. The circuit(s) would be broken, e.g., if the plunger/piston has been moved from an initial, unused position, if an adjacent component has been moved (e.g., to pierce a septum), and/or if the cartridge had been previously installed and removed from an infusion device.

Figure 7A:
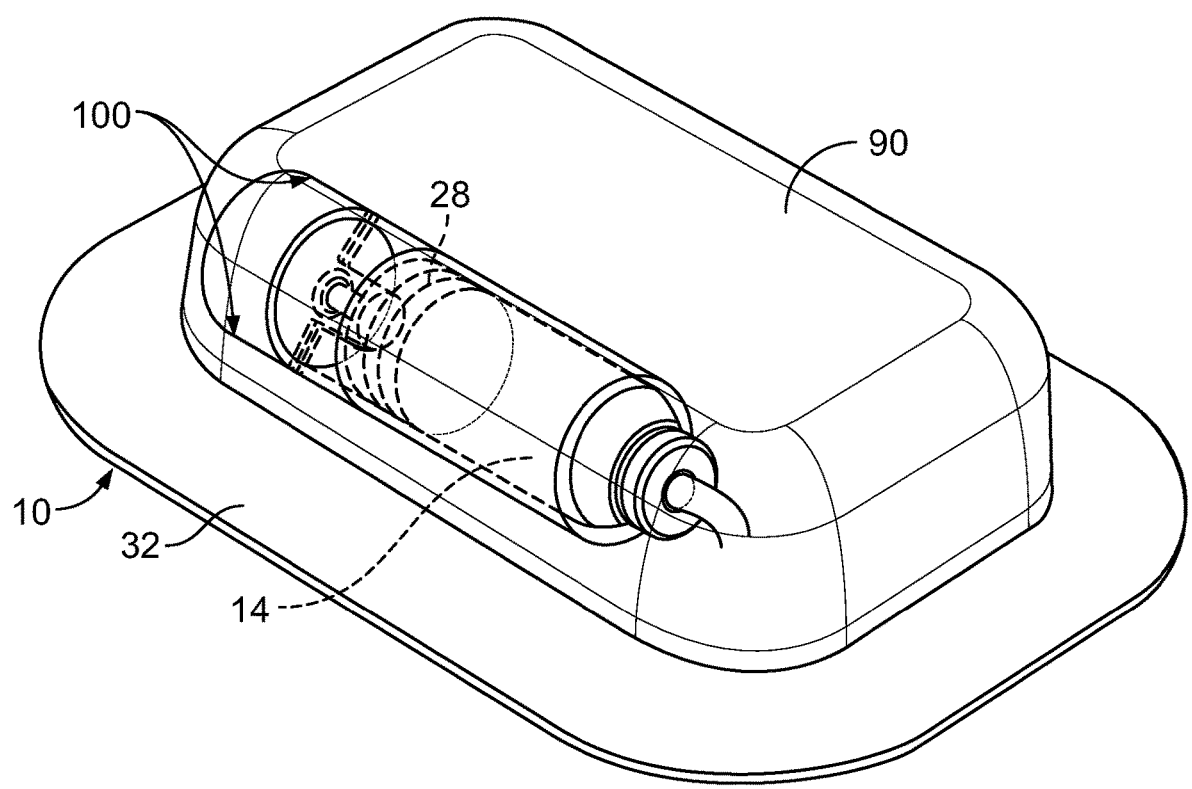
Figure 7B:
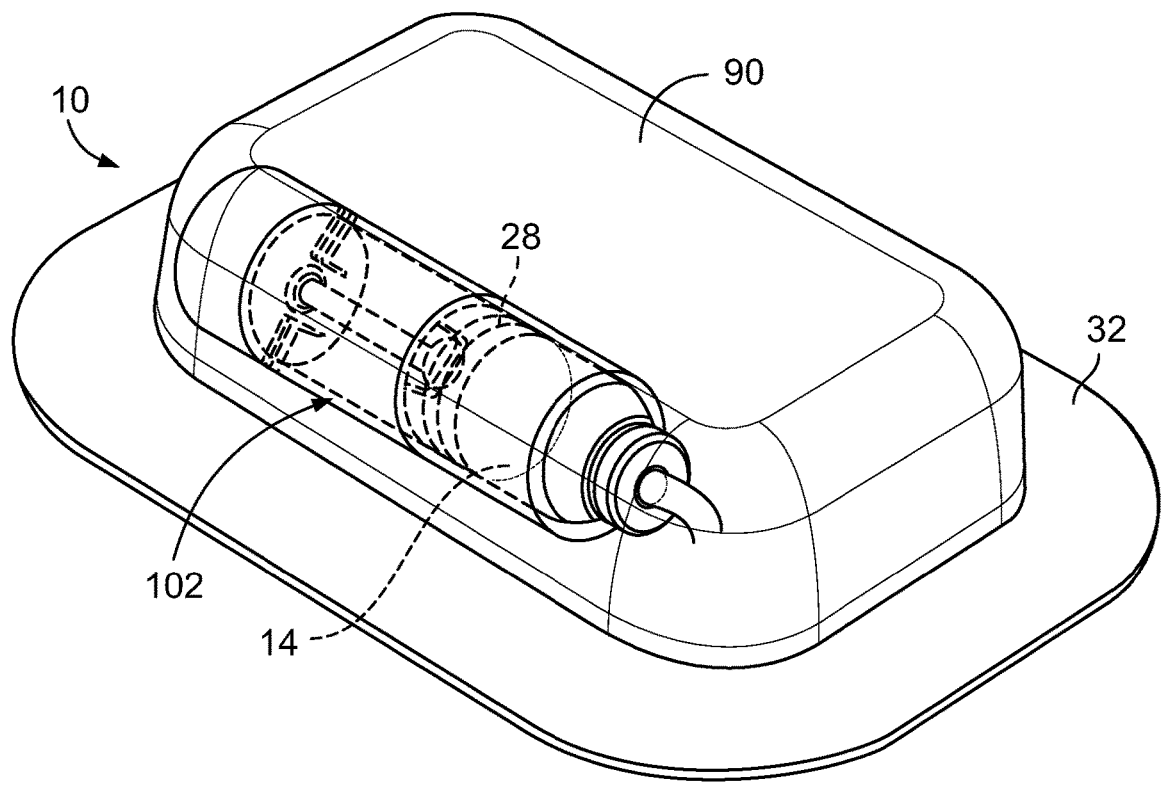
Figure 8A:
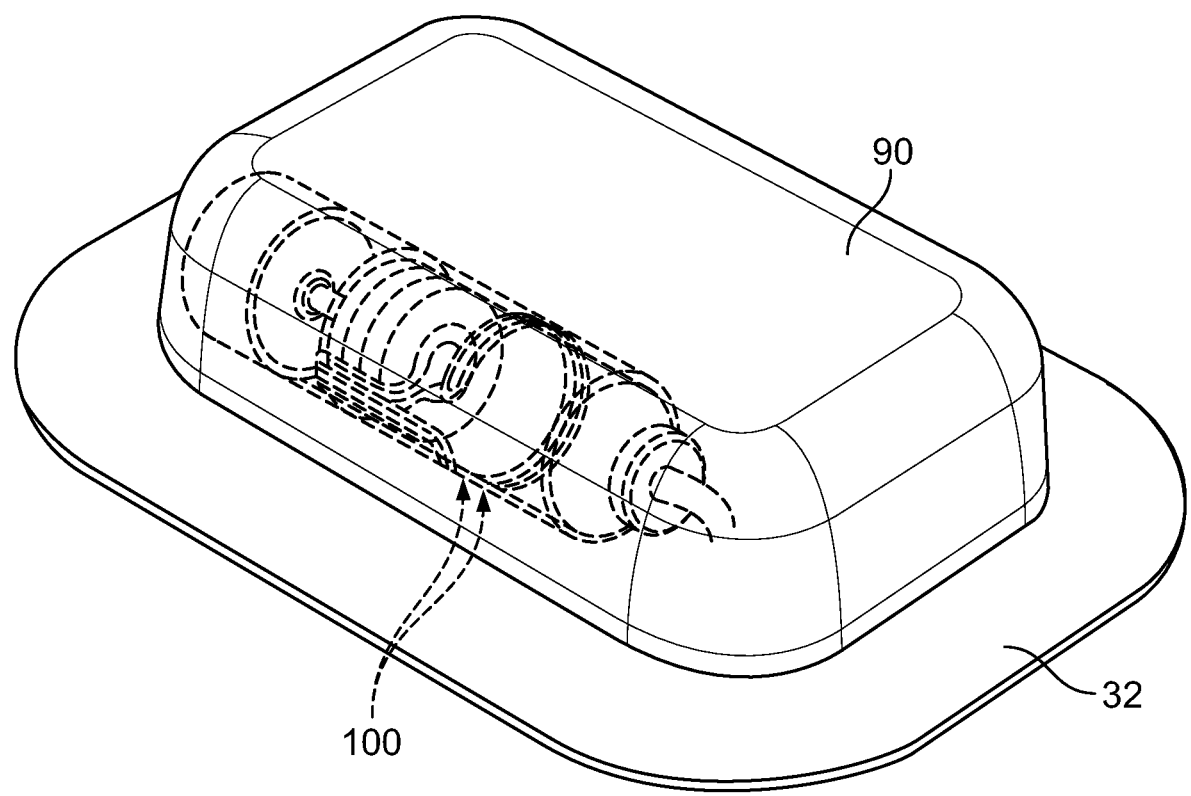
FIGS. 8a and 8b are perspective views of a drug delivery device similar to the drug delivery device of FIGS. 7a and 7b.
Figure 8B:
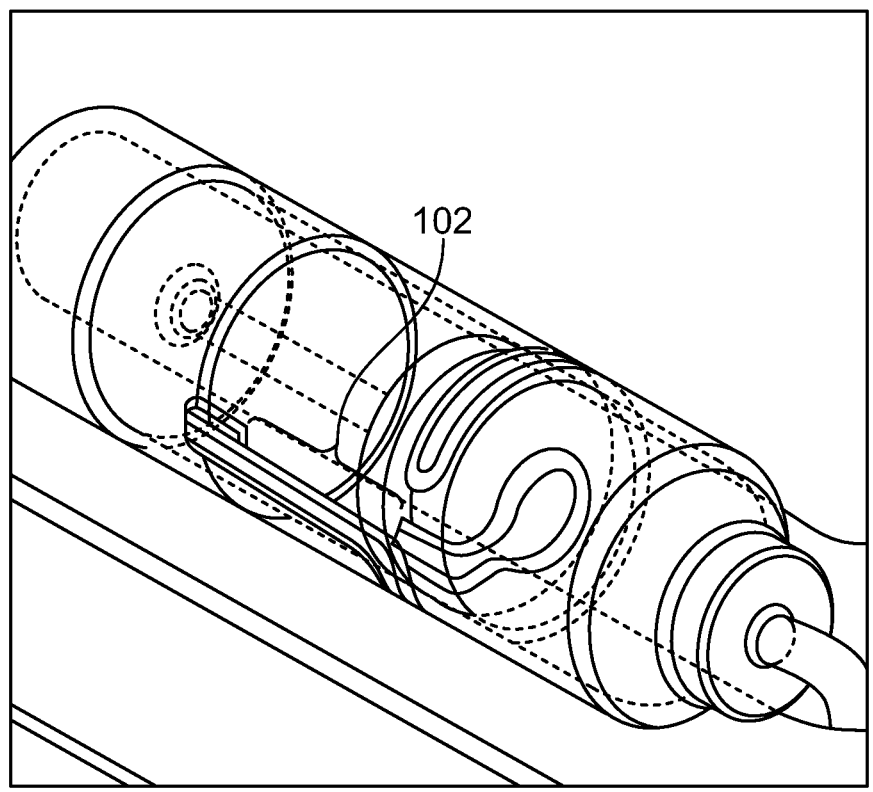

In a first example, and with reference to FIGS. 7a, 7b and FIGS. 8a, 8b, the plunger/piston 28 may be provided with contact points 100 that close a circuit 102 formed on or within the drug chamber/reservoir 14 when the plunger/piston 28 is in its original position (FIG. 7a, FIG. 8a), and with the circuit being broken when the plunger/piston has been moved from its initial position (FIG. 7b, FIG. 8b).

In one embodiment, the circuit 102 is flexible and printed on or otherwise associated to a tearable substrate, optionally including perforations. In one particular embodiment, the circuit 102 may be defined by conductive ink printed on a paper or plastic label. An exemplary circuit 102 is shown in FIG. 9a.

Figure 9A:
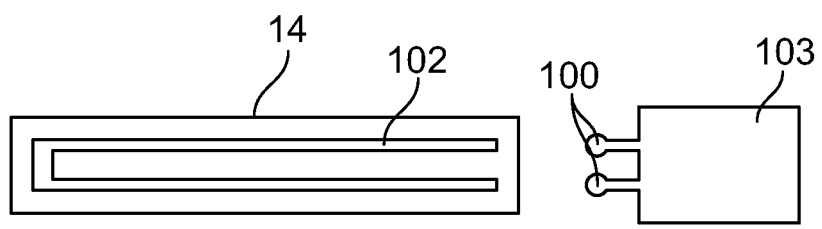
FIGS. 9a, 9b, 9c and 9d schematically depict the reservoir of a drug delivery device and an associated circuit and contact points for closing the circuit, with FIG. 9b showing the circuit being closed and FIGS. 9c and 9d showing different conditions under which the circuit is broken.
Figure 9B:
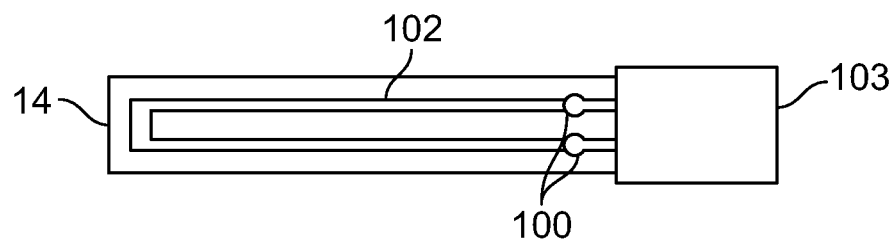

As for the contact points 100 (which are also shown in FIG. 9a), in one embodiment, they are either directly soldered to or remotely connected to a printed circuit board (PCB) 103, which includes, or is connected to, a controller of the main body. FIG. 9a shows the contact points 100 separate from the circuit 102, while FIG. 9b shows the contact points 100 electrically coupled to the circuit 102, thereby closing the circuit. The contact points may be differently configured without departing from the scope of the present disclosure. For example, in one embodiment, the contact points are configured as sliding contacts, such as leaf springs or spring-loaded pins, commonly called "pogo pins."

Figure 9C:
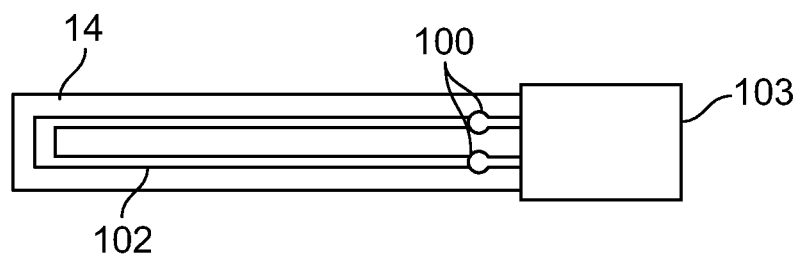
Figure 9D:
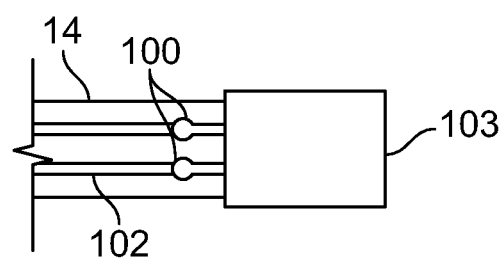

When the circuit of the cartridge is closed or unbroken (as in FIG. 9b), the controller of the main body will detect it. On the other hand, if the circuit is open (as in FIG. 9a) or broken (as in FIGS. 9c and 9d), the controller of the main body sees an open circuit. An open circuit occurs if no sterile cartridge is detected (FIG. 9a), if the substrate for the circuit is partially torn (FIG. 9c), or the substrate for the circuit is fully torn (FIG. 9d), each of which looks the same to the main device, as if a cartridge is not installed at all. In one embodiment, there may be a secondary mechanism for detecting the presence of the cartridge, which could then trigger a check for the presence or absence of circuit continuity, and yield an error message.

Figure 10A:
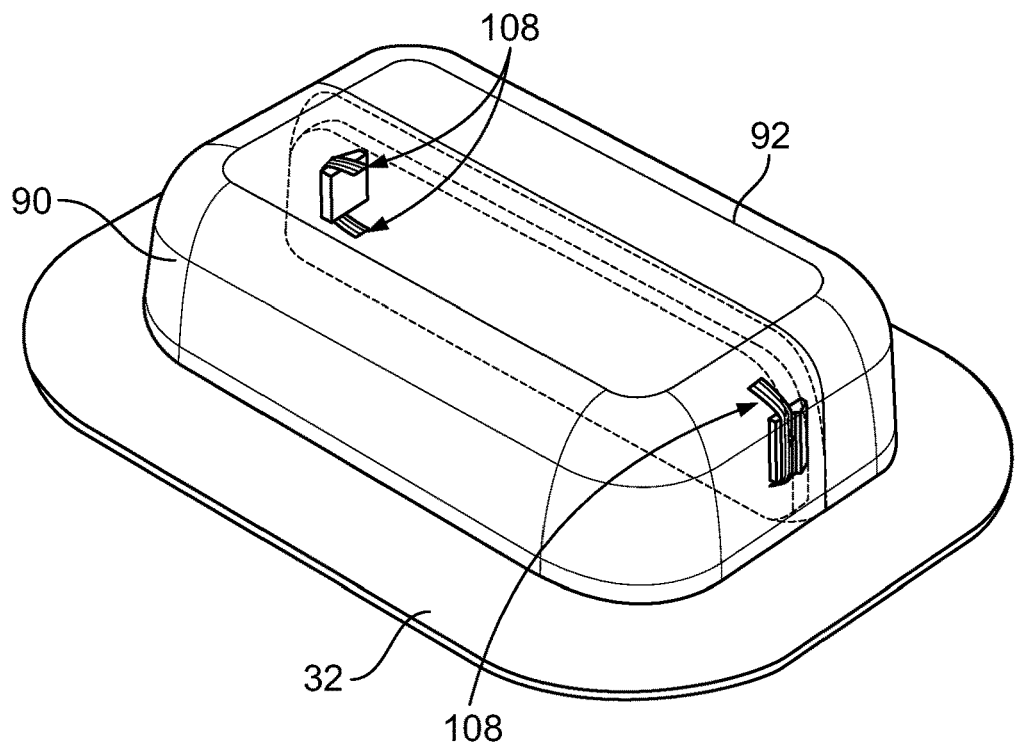
FIGS. 10a, 10b, 10c, 10d and 10e are perspective views of a drug delivery device in which breakable sterility sensor circuits are formed between the cartridge and the main body of the drug delivery device when the cartridge is attached to the main body, as shown in FIG. 10a, and broken when the cartridge is detached from the main body, as shown in FIG. 10b.
Figure 10B:
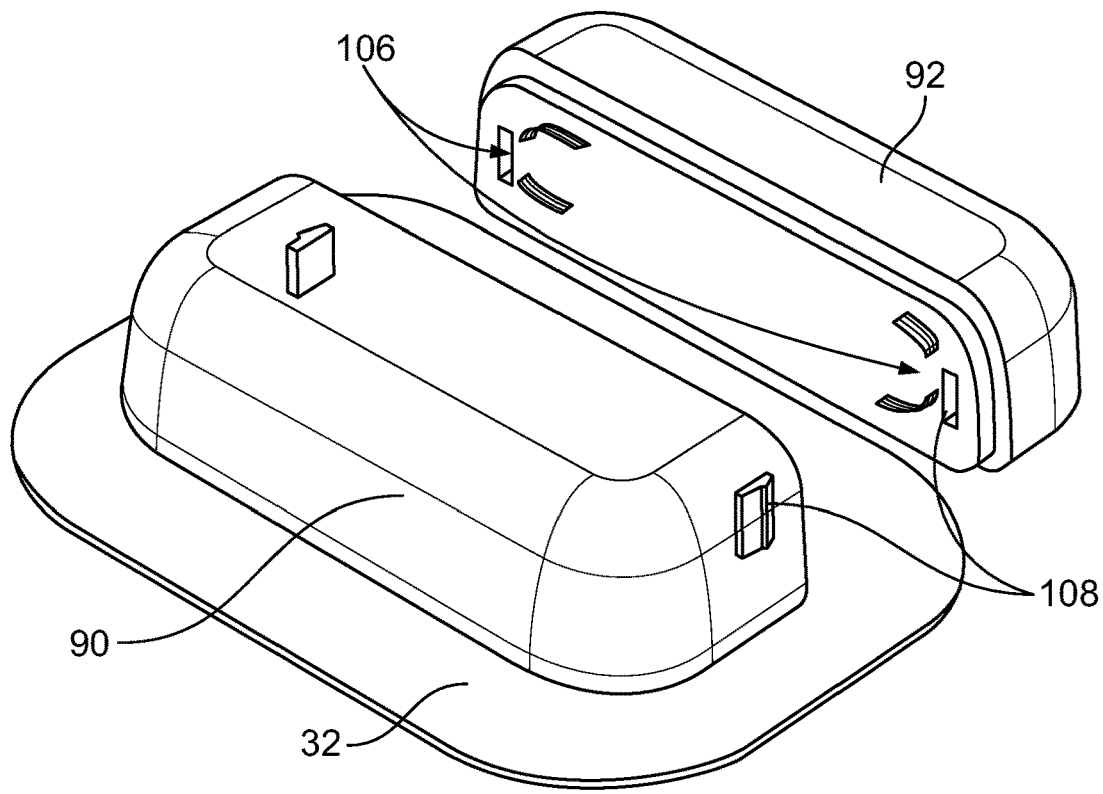
Figure 10C:
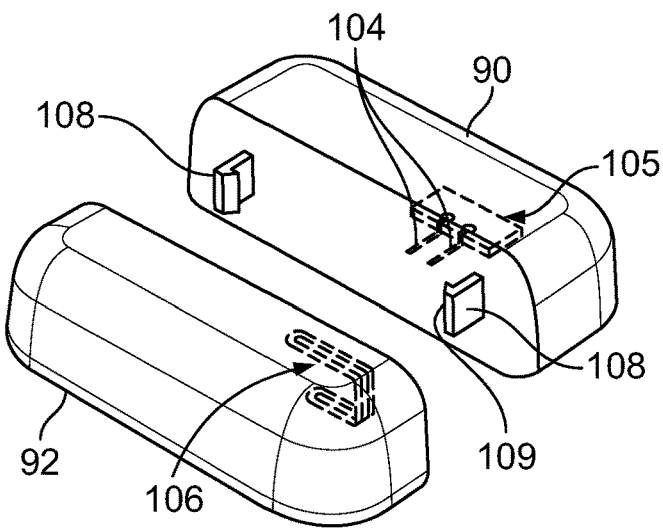
Figure 10D:
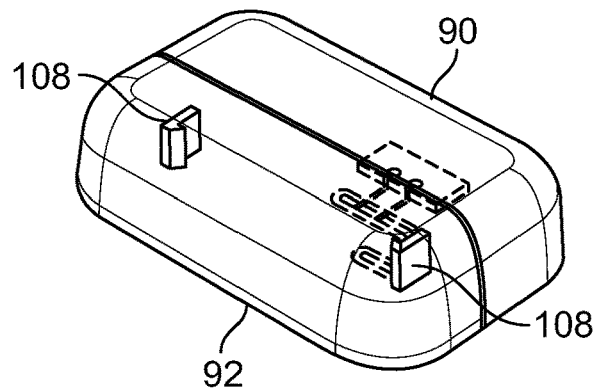
Figure 10E:
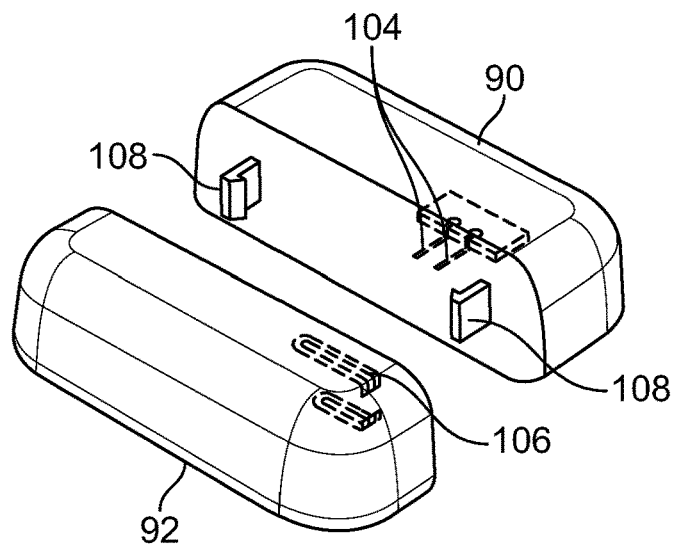

In another embodiment, and with reference to FIGS. 10a-10e, the main body 90 may be provided with contact points 104 of a PCB 105 that are configured to be electrically coupled to a circuit 106 formed on/in the cartridge 92 when a cartridge 92 is attached to the main body 90 (FIGS. 10a and 10d). The circuit 106 is configured to be open before the cartridge 92 is mounted to the main body 90 (FIGS. 10b and 10c) or when a previously-used cartridge 92 is paired to the main body, while being broken at the time that an installed cartridge 92 is detached from the main body 90 (FIG. 10e).

More particularly, in the embodiment of FIGS. 10a-10e, the main body 90 is provided with snap-features 108 that engage complementary snap-features 108 of the cartridge 92 when the main body 90 and cartridge 92 are brought together. As shown in FIGS. 10c and 10d, the circuit 106 is incorporated into the cartridge 92 so as to be present at one or more locations that bring the circuit 106 into engagement with snap-fit features 108 of the main body 90 when the cartridge 92 is associated to the main body 90. This may include one or more portions of the circuit 106 being positioned at or adjacent to one or more of the snap features 108 of the cartridge 92. When an unused cartridge 92 is paired to the main body 90, one or more of the snap-fit features 108 of the main body 90 comes into contact with the circuit 106. The illustrated snap-fit features 108 of the main body 90 are provided with a lip or extension 109 that passes by the circuit 106 during installation of the cartridge 92 to the main body 90. This may be achieved, for example, by provided a flexible circuit 106 that is temporarily displaced by the extension 109 when the cartridge 92 is mounted to the main body 90, with the circuit 106 moving back toward its initial position once the extension 109 has passed by (FIG. 10d).

As can be seen in FIG. 10d, the extension 109 effectively hooks behind or onto the circuit 106, such that subsequent disengagement of the cartridge 92 from the main body 90 will cause the extension 109 to pull and tear through the circuit 106, resulting in a permanently broken circuit 106 (FIG. 10e). If the used cartridge 92 is later mated to the same or a different main body 90 (e.g., if the cartridge 92 is refilled), its circuit 106 will not be able to electrically couple with the contact points 104 of the PCB 105. The controller of the main body 90 (which is coupled to the PCB 105) will be able to determine that the circuit 106 has not been electrically coupled to the PCB 105 and, in response, prevent reuse of the cartridge 92.

Figure 11A:
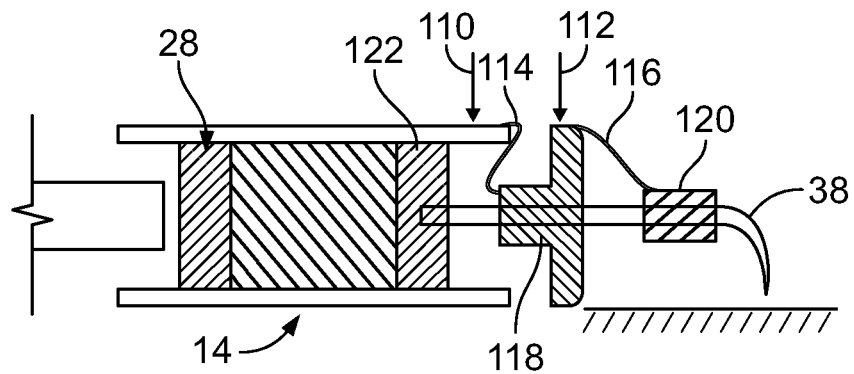
FIGS. 11a, 11b and 11c depict the reservoir of a drug delivery device that may be incorporated into the cartridge with breakable sterility sensor circuits, with the sterility sensor circuits shown as intact in FIG. 11a and broken in FIGS. 11b and 11c.
Figure 11B:
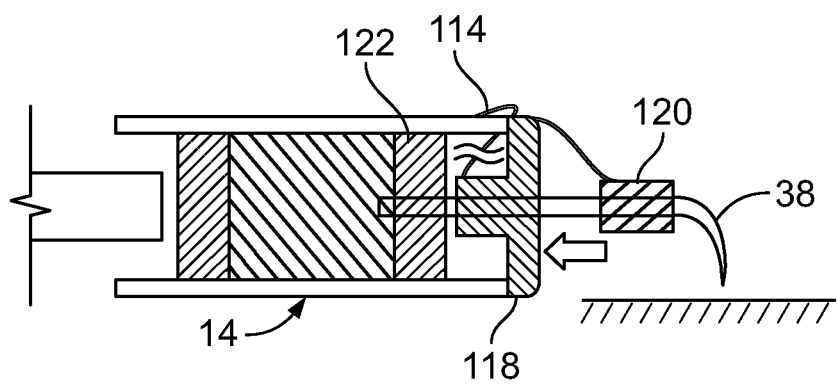
Figure 11C:
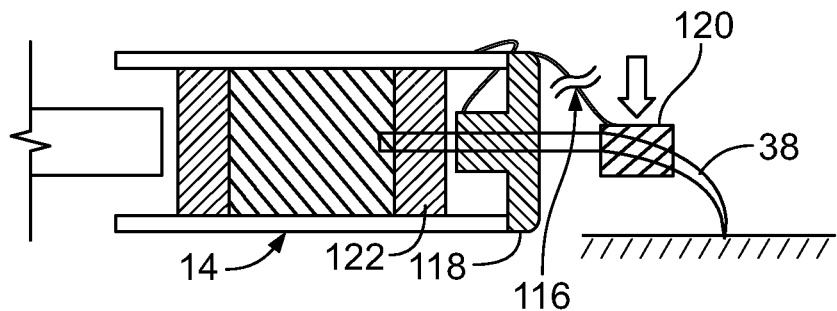

In a third example, and with reference to FIGS. 11a, 11b and 11c, a main body includes contact points 110 and 112 that are electrically coupled to a controller of a main body, such as via a PCB. A mating cartridge includes a pair of circuits 114 and 116 configured to be electrically coupled to the contact points 110 and 112, respectively, upon association of the cartridge to the main body. The first circuit 114 is connected to the drug reservoir 14 of the cartridge and to a first needle holder 118 associated with the needle 38 of the cartridge, while the second circuit 116 is connected to the first needle holder 118 and a second needle holder 120. In preparation for drug delivery, the first needle holder 118 is moved from its initial position (FIG. 11a) toward the drug reservoir 14 to cause the proximal end of the needle 38 to pierce a septum 122 that closes drug reservoir 14 (FIG. 11b). The first circuit 114 is associated to the drug reservoir 14 and the first needle holder 118 such that this movement of the first needle holder 118 toward the drug reservoir 14 causes the circuit 114 to become pinched between the first needle holder 118 and the drug reservoir 14, which causes the circuit 114 to break, as shown in FIG. 11b. Subsequently, the second needle holder 120 is moved away from the first needle holder 118 to cause the distal end of the needle 38 to move toward the skin of the patient (FIG. 11c). The second circuit 116 is associated to the first needle holder 118 and the second needle holder 120 such that this movement of the second needle holder 120 away from the first needle holder 118 causes the circuit 116 to stretch and break, as shown in FIG. 11c.

While FIGS. 11a-11c are shown with two circuits that are broken in preparation for drug delivery, it should be understood that breaking either may be sufficient to render the cartridge unusable after drug delivery has been completed. It should also, thus, be understood that, in other embodiments, it may be sufficient for only one circuit to be provided and broken to signal that a cartridge has been used. As can be appreciated, circuits/contact points may be advantageously associated with other structures in the cartridge/main body that move relative to one another upon use of the cartridge, such that the circuit is broken upon movement from an initial position.

In another aspect of the present disclosure, the infusion device 10 may be provided with a locking system that prevents operation of/deactivates the device if, when a cartridge is attached to the main body, any circuits, such as those described above, are broken. The device would remain inoperable/deactivated until a cartridge with intact circuits is properly attached to the main body. The locking system may be electronic, so that, e.g., upon detection of the attachment to the main body of a cartridge with a broken circuit, the device would not begin any infusion steps. Alternatively, the broken circuits may simply be indicators of the loss of sterility that get checked for continuity by the device, in which case the device would be capable of all functions. Under such circumstances, the controller would assess the state of the circuit(s), and raise a warning and/or move to an error state upon finding a lack of continuity.

Figure 12A:
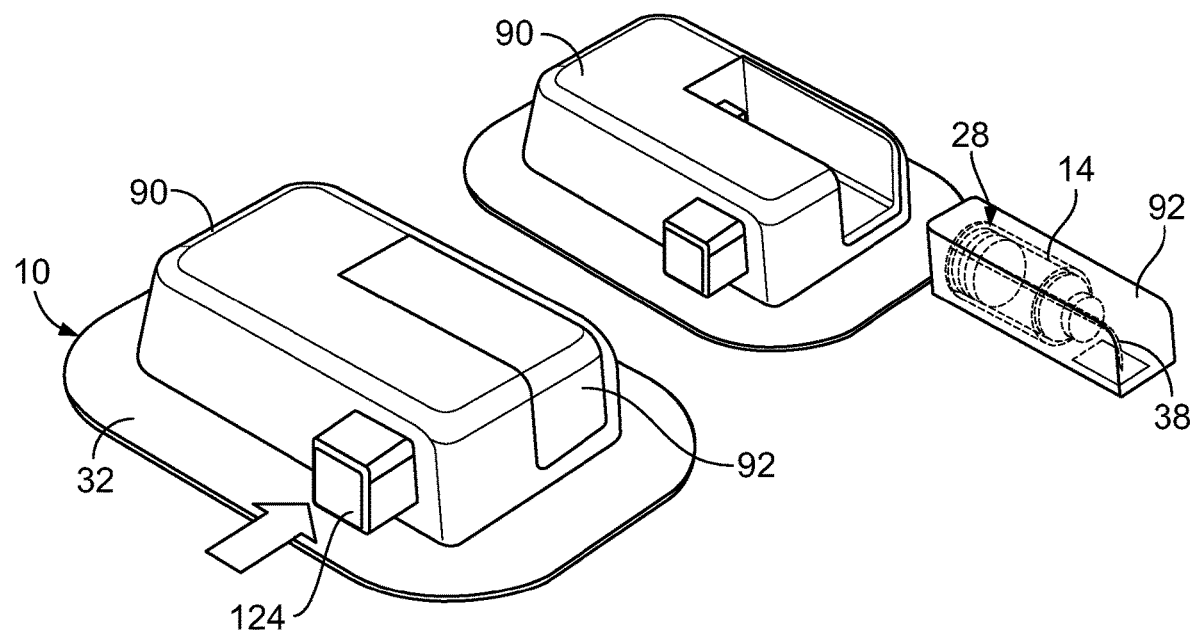
FIGS. 12a, 12b and 12c depict a drug delivery device having a mechanical locking system for preventing operation of the system if, upon attachment of the cartridge to the main body, a sterility sensor circuit is broken.
Figure 12B:
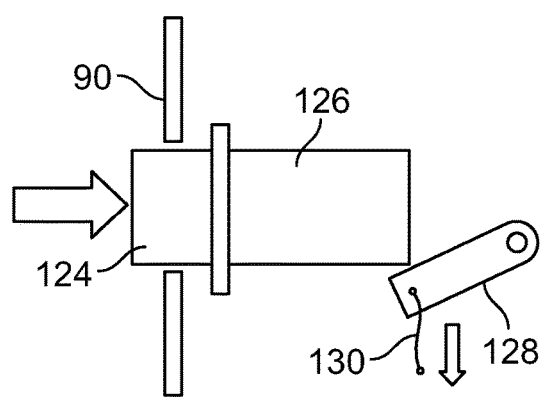
Figure 12C:
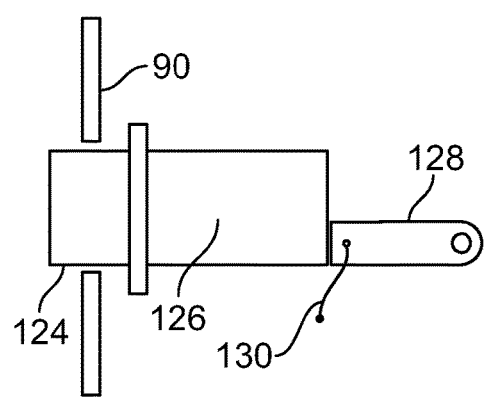

Alternatively, the locking system could be in the form of a mechanical lock that, when actuated, blocks movement of a component of the device that is moved during operation. By way of example, and with reference to FIG. 12a, the infusion device 10 is provided with a push button 124 that extends through an opening in the main body 90 and is used to actuate the needle 38. As seen in FIGS. 12b and 12c, the push button 124 is formed as part of an elongated shaft 126 that extends into the interior of the main body 90. When the button 124 is pushed, the shaft 126 will move inwardly so that its end will engage a mechanism (not shown) for actuating the needle so as to cause the needle to engage the patient. A latch 128 is pivotally mounted on the interior of the housing 90 to which a memory/muscle wire 130 is secured. If the sterility sensor circuits are intact, current is delivered to the memory wire 130 to contract the wire to maintain the latch 128 in a position in which it will not interfere with movement of the push button 124 (FIG. 12b). On the other hand, if a sterility sensor circuit is broken, current will not be delivered to the memory wire 130, and the wire will relax, thus pivoting the latch 128 into a position where it blocks movement of the push button 124 (FIG. 12c).

Upon triggering of the locking system, an alert may also be provided to the healthcare provider and/or the patient by, e.g., the infusion device providing a tactile, visual and/or audible signal, or by providing notification on, e.g., a cell phone through an app connecting the infusion device to the cell phone.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An on-body drug delivery device comprising:
   a main body including a fluid flow path and a housing defining a body interface;
   an adhesive pad associated with a lower surface of the housing and configured to be removably attached to a human body surface;
   a cartridge removably attachable to the main body and including a fillable drug chamber having an outlet and a seal configured to be opened upon the cartridge being attached to the main body so as to place the fluid flow path into fluid communication with the outlet;
   a needle fluidically connected to the fluid flow path; and
   a controller configured to execute a drug delivery routine, wherein the cartridge further includes
   a cartridge housing defining a cartridge interface configured to be associated to the body interface upon the cartridge being attached to the main body,
   a piston received in the drug chamber movable from a first, initial position to a second position to convey a drug from the drug chamber to the needle during said drug delivery routine,
   an actuation device for moving the piston from the first position to the second position, and
   at least one breakable sterility sensor circuit formed by attachment of the cartridge to the main body, the at least one breakable sterility circuit being
      closed when the cartridge is properly attached to the main body,
      open when the cartridge is not properly attached to the main body, and
      broken when the cartridge is removed from the main body after being properly attached thereto and/or when the piston is not in the initial position when the cartridge is first attached to the main body.

2. The on-body drug delivery device of claim 1 wherein the piston further comprises one or more contact points that close the at least one breakable sterility sensor circuit when the piston is in the initial position.

3. The on-body drug delivery device of claim 2 wherein the drug delivery device is further configured to cause a signal to be emitted when the at least one breakable sterility sensor circuit is broken.

4. The on-body drug delivery device of claim 3 wherein the signal is one or more of a tactile signal, an audible signal or a visual signal that is emitted by the drug delivery device.

5. The on-body drug delivery device of claim 2 further comprising a lock actuated when the at least one breakable sterility sensor circuit is broken to prevent operation of the drug delivery device.

6. The on-body drug delivery device of claim 1 further comprising a lock actuated when the at least one breakable sterility sensor circuit is broken to prevent operation of the drug delivery device.

7. The on-body drug delivery device of claim 6 wherein the drug delivery device is further configured to cause a signal to be emitted when the at least one breakable sterility sensor circuit is broken.

8. The on-body drug delivery device of claim 1 wherein the drug delivery device is further configured to cause a signal to be emitted when the at least one breakable sterility sensor circuit is broken.

9. The on-body drug delivery device of claim 8 wherein the signal is one or more of a tactile signal, an audible signal or a visual signal that is emitted by the drug delivery device.

10. The on-body drug delivery device of claim 8 wherein the device is configured to cause the signal to be emitted by a separate device.

11. The on-body drug delivery device of claim 10 wherein the separate device is a cell phone.

12. The on-body drug delivery device of claim 1 further comprising a spring-loaded latch for securing the cartridge to the housing.

13. The on-body drug delivery device of claim 12 wherein the spring-loaded latch is locked-out during operation of the device.

14. The on-body drug delivery device of claim 1 further comprising snap-fit structures for securing the cartridge to the main body.

15. The on-body drug delivery device of claim 14 wherein the at least one breakable sterility sensor circuit and/or contact points are associated with the snap-fit structures.

16. The on-body drug delivery device of claim 1 further comprising the needle mounted to a movable needle holder and in which the at least one breakable sterility sensor circuit and/or a contact point is associated with the needle holder.

17. The on-body drug delivery device of claim 1 further comprising first and second breakable sterility sensor circuits, the needle mounted to first and second needle holders, the first needle holder for moving the needle so as to pierce a septum interior of the drug chamber and the second needle holder for moving the needle to engage with a patient, the first breakable sterility sensor circuit associated with the first needle holder and the second breakable sterility sensor circuit associated with the second needle holder.

18. The on-body drug delivery device of claim 1 further comprising a push button for actuating the needle, the push button extending through an opening in the housing, and a latch pivotally mounted on an interior of the housing and selectively engageable with the button to permit or prevent actuation of the needle.

19. The on-body drug delivery device of claim 18 further comprising a memory wire associated with the latch and connected to a source of current for moving the latch between a first position to permit movement of the push button and a second position to prevent movement of the push button.

20. The on-body drug delivery device of claim 1 wherein the fillable drug chamber contains pegfilgrastim.

21. The on-body drug delivery device of claim 1 wherein the device is configured to communicate wirelessly with a separate device.

22. The on-body drug delivery device of claim 1 wherein the device is configured to communicate wirelessly with a separate device of a patient.

23. The on-body drug delivery device of claim 1 wherein the device is configured to communicate wirelessly with a separate device of a healthcare provider.

24. An on-body drug delivery device comprising:
a main body including a fluid flow path and a housing defining a body interface;
an adhesive pad associated with a lower surface of the housing and configured to be removably attached to a human body surface;
a cartridge removably attachable to the main body and including a fillable drug chamber having an outlet and a seal configured to be opened by attachment of the cartridge to the main body so as to place the fluid flow path into fluid communication with the outlet;
a needle fluidically connected to the fluid flow path; and
a controller configured to execute a drug delivery routine,
wherein the cartridge further includes
a cartridge housing defining a cartridge interface configured to be associated to the body interface upon the cartridge being attached to the main body,
a piston received in the drug chamber movable from a first, initial position to a second position to convey a drug from the drug chamber to the needle during said drug delivery routine,
an actuation device for moving the piston from the first position to the second position, and
at least one breakable sterility sensor circuit formed by attachment of the cartridge to the main body, the at least one breakable sterility circuit being at least one breakable sterility sensor circuit formed by attachment of the cartridge to the main body, the at least one breakable sterility circuit being
closed when the cartridge is properly attached to the main body,
open when the cartridge is not properly attached to the main body, and
broken when the cartridge is removed from the main body after being properly attached thereto and/or when the piston is not in the initial position when the cartridge is first attached to the main body.

25. An on-body drug delivery device comprising:
a main body including a fluid flow path and a housing defining a body interface;
an adhesive pad associated with a lower surface of the housing and configured to be removably attached to a human body surface;
a cartridge removably attachable to the main body and including a fillable drug chamber having an outlet and a seal configured to be automatically opened upon the cartridge being attached to the main body so as to place the fluid flow path into fluid communication with the outlet;
a needle fluidically connected to the fluid flow path; and
a controller configured to execute a drug delivery routine,
wherein the cartridge further includes
a cartridge housing defining a cartridge interface configured to be associated to the body interface upon the cartridge being attached to the main body,
a piston received in the drug chamber movable from a first, initial position to a second position to convey a drug from the drug chamber to the needle during said drug delivery routine,
an actuation device for moving the piston from the first position to the second position, and
at least one breakable sterility sensor circuit formed by attachment of the cartridge to the main body, the at least one breakable sterility circuit being
closed when the cartridge is properly attached to the main body,
open when the cartridge is not properly attached to the main body, and
broken when the cartridge is removed from the main body after being properly attached thereto and/or when the piston is not in the initial position when the cartridge is first attached to the main body.

* * * * *